United States Patent
Park et al.

(10) Patent No.: US 10,343,184 B2
(45) Date of Patent: Jul. 9, 2019

(54) METHOD OF MANUFACTURING POLYMER-FREE EVEROLIMUS-ELUTING CORONARY STENT FABRICATED BY ELECTROSPINNING TECHNIQUE

(71) Applicant: CHONNAM NATIONAL UNIVERSITY HOSPITAL, Gwangju (KR)

(72) Inventors: Dae Sung Park, Gwangju (KR); In-Ho Bae, Gwangju (KR); Jae Won Shim, Gwangju (KR); So Youn Lee, Gwangju (KR); Eun Jae Jang, Gwangju (KR); Kyung Seob Lim, Gwangju (KR); Jun Kyu Park, Gwangju (KR); In Soo Kim, Gwangju (KR); Doo Sun Sim, Gwangju (KR); Myung Ho Jeong, Gwangju (KR)

(73) Assignee: CHONNAM NATIONAL UNIVERSITY HOSPITAL, Gwangju (KR)

( * ) Notice: Subject to any disclaimer, the term of this patent is extended or adjusted under 35 U.S.C. 154(b) by 0 days.

(21) Appl. No.: 15/715,635

(22) Filed: Sep. 26, 2017

(65) Prior Publication Data
US 2018/0015500 A1    Jan. 18, 2018

Related U.S. Application Data

(62) Division of application No. 15/250,104, filed on Aug. 29, 2016, now Pat. No. 9,795,987.

(30) Foreign Application Priority Data

May 31, 2016 (KR) .......................... 10-2016-0067475

(51) Int. Cl.
| | | |
|---|---|---|
| *B05D 1/00* | (2006.01) | |
| *A61F 2/82* | (2013.01) | |
| *C23C 16/40* | (2006.01) | |
| *C23C 16/50* | (2006.01) | |

(Continued)

(52) U.S. Cl.
CPC ................ *B05D 1/007* (2013.01); *A61F 2/82* (2013.01); *A61L 31/088* (2013.01); *A61L 31/16* (2013.01);

(Continued)

(58) Field of Classification Search
CPC ...... A61K 31/7048; A61M 25/10; A61F 2/82; B05D 3/00

(Continued)

(56) References Cited

U.S. PATENT DOCUMENTS

2004/0170685 A1*  9/2004  Carpenter ............ A61K 31/685
                                                           424/468
2008/0004691 A1   1/2008  Weber
(Continued)

FOREIGN PATENT DOCUMENTS

| KR | 10-1116673 | 2/2012 |
|---|---|---|
| KR | 10-1198464 | 10/2012 |
| KR | 1020150145398 | 12/2015 |

*Primary Examiner* — Dah-Wei D. Yuan
*Assistant Examiner* — Andrew J Bowman
(74) *Attorney, Agent, or Firm* — Hauptman Ham, LLP

(57) ABSTRACT

Provided is a drug-eluting coronary stent. In the drug-eluting coronary stent according to the present invention, electrospinning is used, thereby making it possible to precisely control a total content of an everolimus-based drug bound thereto and form a uniform layer in spite of not using a polymer causing late thrombosis, or the like.

7 Claims, 3 Drawing Sheets

(51) Int. Cl.
   *A61L 31/08* (2006.01)
   *A61L 31/16* (2006.01)
   *C23C 16/505* (2006.01)
   *C23C 16/56* (2006.01)

(52) U.S. Cl.
   CPC .............. *B05D 1/005* (2013.01); *C23C 16/40* (2013.01); *C23C 16/405* (2013.01); *C23C 16/50* (2013.01); *C23C 16/505* (2013.01); *C23C 16/56* (2013.01); *A61F 2240/001* (2013.01); *A61F 2250/0067* (2013.01); *A61L 2300/416* (2013.01); *B05D 2202/00* (2013.01); *B05D 2254/00* (2013.01)

(58) Field of Classification Search
   USPC ....... 424/468; 623/1.42; 427/2.25, 2.1, 2.26, 427/2.24
   See application file for complete search history.

(56) References Cited

U.S. PATENT DOCUMENTS

| | | |
|---|---|---|
| 2009/0286761 A1 | 11/2009 | Cheng |
| 2010/0034862 A1 | 2/2010 | Laronde |
| 2010/0272778 A1 | 10/2010 | McClain |
| 2011/0009954 A1* | 1/2011 | Cho .................. A61L 31/022 623/1.42 |
| 2012/0165922 A1* | 6/2012 | Gong .................. B05D 3/107 623/1.42 |
| 2014/0018908 A1 | 1/2014 | Kwon |
| 2015/0182732 A1* | 7/2015 | Zeng .................. A61L 29/14 604/103.02 |

* cited by examiner

【FIG. 1】
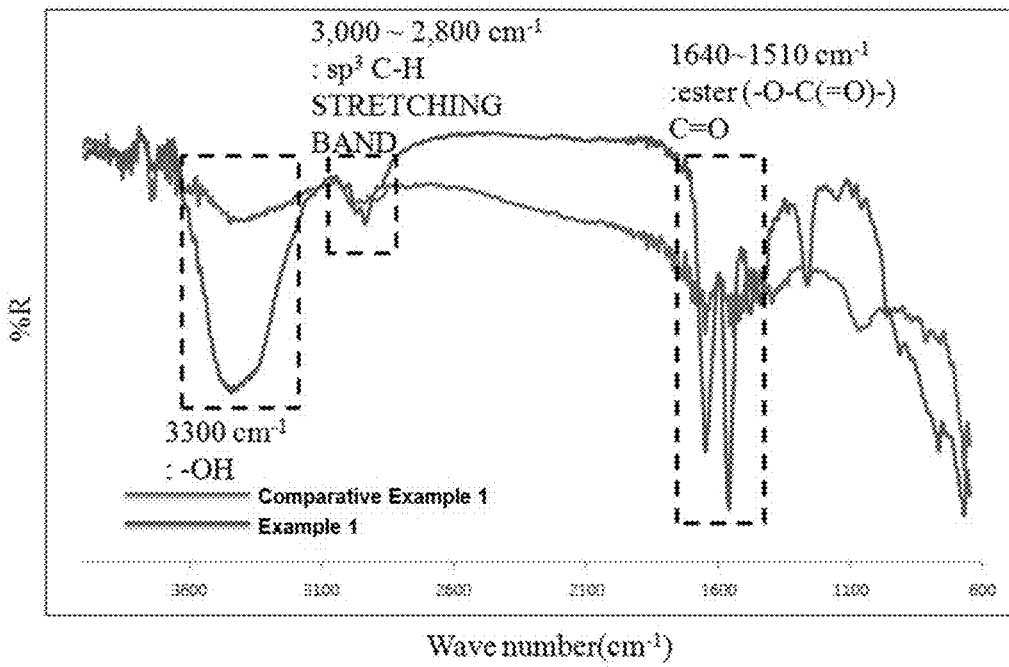
【FIG. 2】
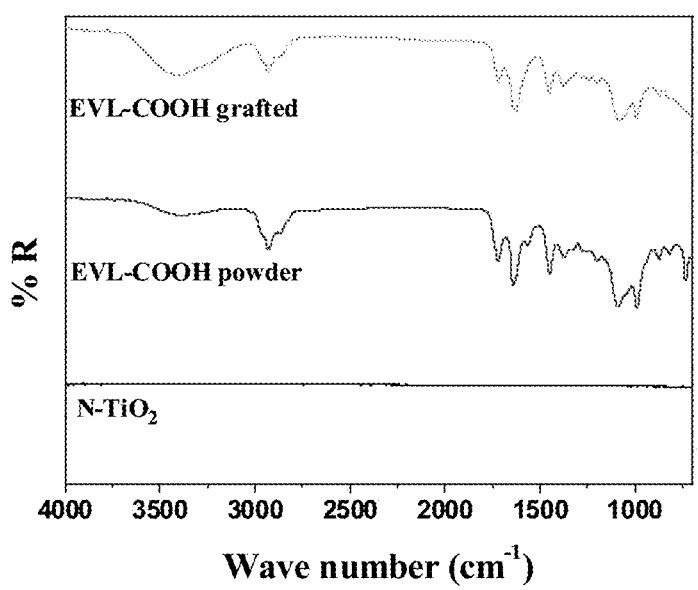

[FIG. 3]
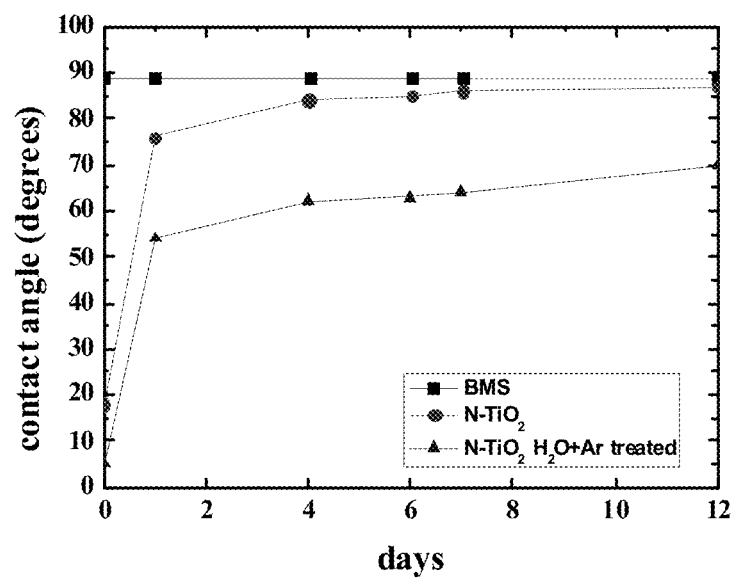

[FIG. 4]
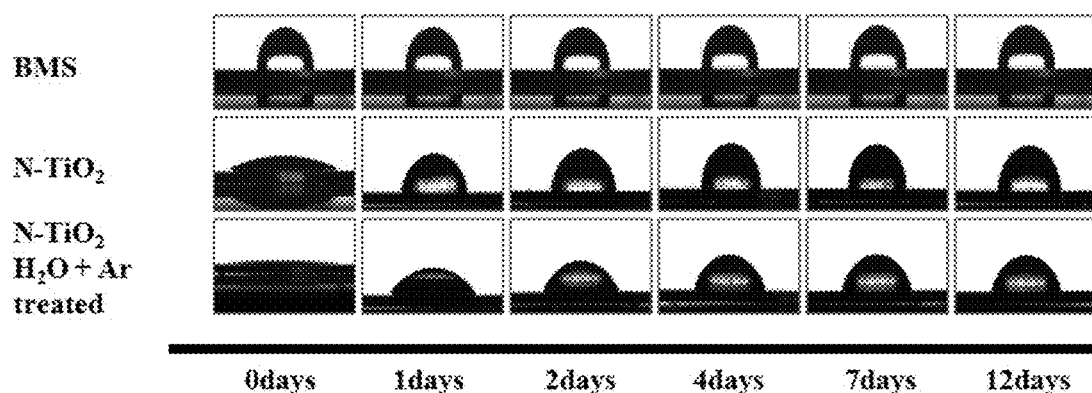
[FIG. 5]
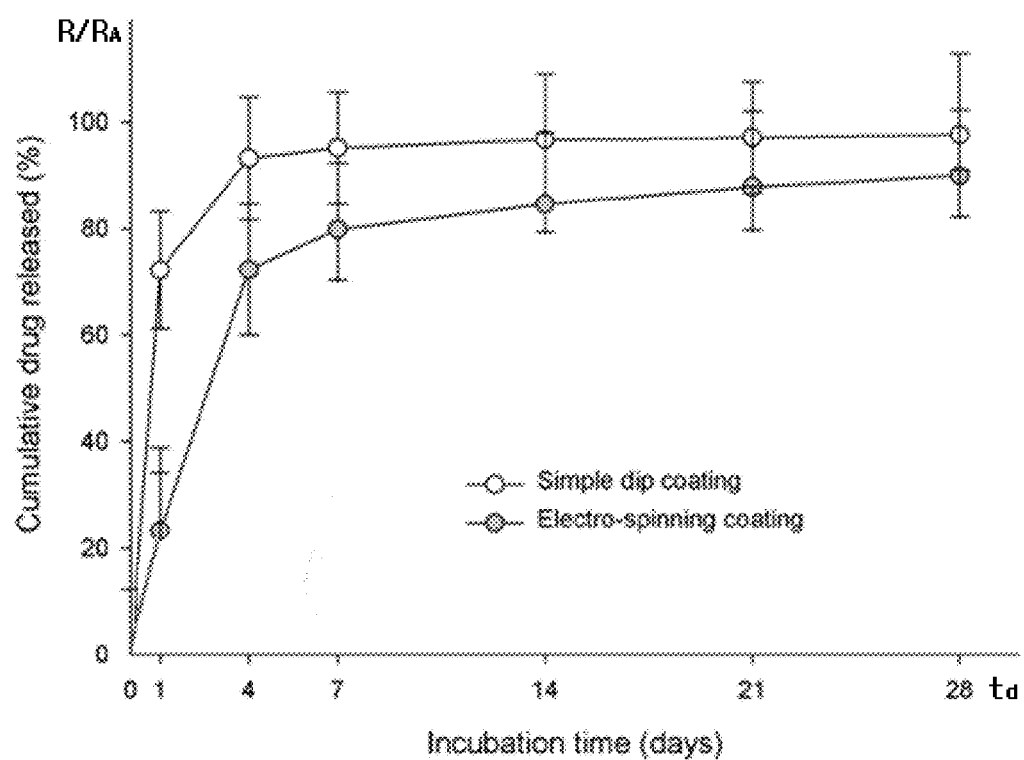

METHOD OF MANUFACTURING POLYMER-FREE EVEROLIMUS-ELUTING CORONARY STENT FABRICATED BY ELECTROSPINNING TECHNIQUE

CROSS-REFERENCE TO RELATED APPLICATIONS

This application claims priority under 35 U.S.C. § 119 to Korean Patent Application No. 10-2016-0067475, filed on Mar. 31, 2016, in the Korean Intellectual Property Office, the disclosure of which is incorporated herein by reference in its entirety.

TECHNICAL FIELD

The following disclosure relates to a drug-eluting coronary stent for preventing problems such as restenosis, and the like.

BACKGROUND

A vascular stent is a medical device used in a blood vessel to expand the blood vessel when the blood vessel becomes narrow due to various diseases occurring in a human body and thus blood circulation disorder, and the like, Occurs. Therefore, a raw material constituting the stent should have particularly high biocompatibility with a human body and stability in addition to mechanical properties such as flexibility, and the like, for insertion in a complicated and curved blood vessel at the time of an operation.

However, when a predetermined time elapses after a stent operation, restenosis frequently occurs due to accumulation of blood clots and fat inside the stent. Recently, as a method for suppressing restenosis, a drug-eluting stent (DES) coated with a small amount of a drug capable of suppressing cell growth to thereby continuously release the drug was developed. Representative examples of the drug-eluting stent include a paclitaxel-eluting stent (TAXUS™), a sirolimus-eluting stent (Cypher™), everolimus-eluting stent, (XIENCE PRIME, Abbott) (here, sirolimus and everolimus are immunosuppressants), and the like. However, there were still problems to be solved such as inflammation due to use of a polymer, late thrombosis, and the like.

A technology of manufacturing a drug-eluting stent may be classified depending on a method of loading a drug on a stent. For example, there are a method of directly attaching the drug to a metal stent, a method of loading the drug in pores of a porous metal stent, a method of binding the drug to a polymer coated on the stent, and the like, and currently, various researches into the methods have been conducted.

The method of binding the drug to the polymer coated on the stent has an advantage in that since the drug is bound to the polymer, release of the drug is delayed and thus, restenosis may be suppressed or delayed, but the method causes a local acidic environment due to a polymer decomposition or swelling phenomenon generated in a drug elution process by various enzymes in blood vessels, solvents, and the like. This causes other side effects such as late thrombosis, suppression of re-endothelialization, and the like.

Recently, various researches into the drug-eluting stent using everolimus, which is a drug suppressing proliferation and having an excellent immunosuppressive effect to thereby be mainly used to manufacture the drug-eluting stent, have been conducted.

However, there are still various technical difficulties in a stent capable of inducing sustained release of a drug by stably maintaining binding of everolimus without deterioration of chemical stability of everolimus and a technology of manufacturing the stent.

RELATED ART DOCUMENT

Patent Document

Korean Patent Laid-Open Publication No. 10-2015-0145398 (Dec. 30, 2015)

SUMMARY

An embodiment of the present invention is directed to providing a drug-eluting coronary stent capable of effectively binding to an everolimus-based drug to the stent to stably and continuously release the everolimus-based drug for a long period of time without using a polymer capable of causing various side effects such as late thrombosis, local inflammation, suppression of re-endothelialization, and the like, and a method of manufacturing the same.

Another embodiment of the present invention is directed to providing a drug-eluting coronary stent capable of precisely controlling a total content of an everolimus-based drug to be loaded and forming a more uniform layer, and a method of manufacturing the same.

Another embodiment of the present invention is directed to providing a drug-eluting coronary stent capable of stably maintaining binding of an everolimus-based drug without deterioration of chemical stability of the everolimus-based drug, and a method of manufacturing the same.

Another embodiment of the present invention is directed to providing a drug-eluting coronary stent capable of preventing initial excessive drug release and adjusting a sustained drug release behavior for a long period of time by precisely controlling a total content of an everolimus-based drug bound onto the stent via an ester bond, and a method of manufacturing the same.

Another embodiment of the present invention is directed to providing a drug-eluting coronary stent capable of significantly increasing a total content of an everolimus-based drug bound onto the stent via an ester bond to minimize a fatal side effect that an effect of the drug is not exhibited due to rapid deterioration of a drug release effect, even though a long period of time elapses, and a method of manufacturing the same.

Another embodiment of the present invention is directed to providing a drug-eluting coronary stent capable of effectively binding an everolimus-based drug to a surface of a titanium oxide layer via an ester bond through a simple process, and a method of manufacturing the same.

In one general aspect, a drug-eluting stent includes: a stent; a nitrogen-doped titanium oxide layer formed on the stent; and a surface-binding functional group formed on the nitrogen-doped titanium oxide layer; and an everolimus-based drug bound to the surface-binding functional group.

The everolimus-based drug and the surface-binding functional group may be covalently bound to each other.

The everolimus-based drug may be bound to the surface-binding functional group by electrospinning.

The surface-binding functional group may be formed on the nitrogen-doped titanium oxide layer by surface treatment with low-temperature plasma.

In another general aspect, a method of manufacturing a drug-eluting stent includes: electrospinning an everolimus-based drug on a nitrogen-doped titanium oxide layer on which a surface-binding functional group is formed to form a covalent bond between the everolimus-based drug and the surface-binding functional group.

The surface-binding functional group may be introduced onto the nitrogen-doped titanium oxide layer formed on a surface of the stent by surface-modification using low-temperature plasma.

The surface-binding functional group may include a hydroxyl group, and the everolimus-based drug may include a carboxylic acid group at an end thereof.

The method of manufacturing a drug-eluting stent may further include introducing the carboxylic acid group at the end of the everolimus-based drug.

The covalent bond may be an ester bond.

BRIEF DESCRIPTION OF THE DRAWINGS

FIG. 1 is a graph illustrating data obtained by measuring surfaces of drug-eluting stents according to Example 1 and Comparative Example 1 using Fourier transform infrared spectroscopy (FT-IR/ATR).

FIG. 2 is a graph illustrating data obtained by measuring the surface of the drug-eluting stent according to Example 1 and an everolimus-based drug powder represented by Chemical Formula 2 using FT-IR/ATR.

FIG. 3 is a graph illustrating contact angles of surfaces of an initially untreated Co—Cr alloy stent (BMS), a titanium oxide layer-coated stent (N—TiO$_2$), and a surface-modified stent (N—TiO$_2$H$_2$O+Ar treated) in Example 1 with respect to water, and FIG. 4 is images indicating the contact angles.

FIG. 5 is a graph illustrating results obtained by measuring amounts of the everolimus-based drug eluted from the drug-eluting stents according to Example 1 and Comparative Example 1 per unit time (day).

DETAILED DESCRIPTION OF EMBODIMENTS

Hereinafter, a drug-eluting coronary stent according to the present invention will be described in detail with reference to the accompanying drawings.

The following accompanying drawings in the present specification are provided by way of example so that the idea of the present invention can be sufficiently transferred to those skilled in the art to which the present invention pertains. Therefore, the present invention is not limited to the drawings provided below but may be specified in a different form.

A description for the known function and configuration unnecessarily obscuring the gist of the present invention will be omitted in the following description and the accompanying drawings.

In addition, unless particularly described, "%" used herein refers to "wt %".

A drug-eluting stent according to an exemplary embodiment of the present invention includes: a stent; a nitrogen-doped titanium oxide layer formed on the stent; and a surface-binding functional group formed on the nitrogen-doped titanium oxide layer; and an everolimus-based drug bound to the surface-binding functional group. Here, the everolimus-based drug and the surface-binding functional group may be covalently bound to each other.

The nitrogen-doped titanium oxide layer may be, for example, a coating layer in which a compound represented by TiO$_2$$_{-x}$N$_x$ is formed on a surface of the stent, wherein x may be in a range of 0.001 to 1. A crystal structure of the titanium oxide layer is not particularly limited. For example, the titanium oxide layer may have various crystal structures such as a rutile crystal structure, an anatase crystal structure, a brookite crystal structure, and the like.

According to the exemplary embodiment of the present invention, the everolimus-based drug may include any one or more selected from everolimus and derivatives thereof. For example, everolimus may be a compound represented by the following Chemical Formula 1.

[Chemical Formula 1]

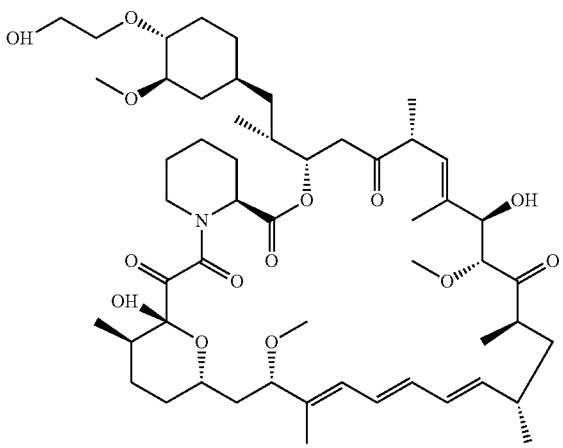

In addition, the everolimus-based drug may include an everolimus derivative including a carboxylic acid group at an end thereof. For example, the everolimus-based drug may be a compound represented by the following Chemical Formula 2.

[Chemical Formula 2]

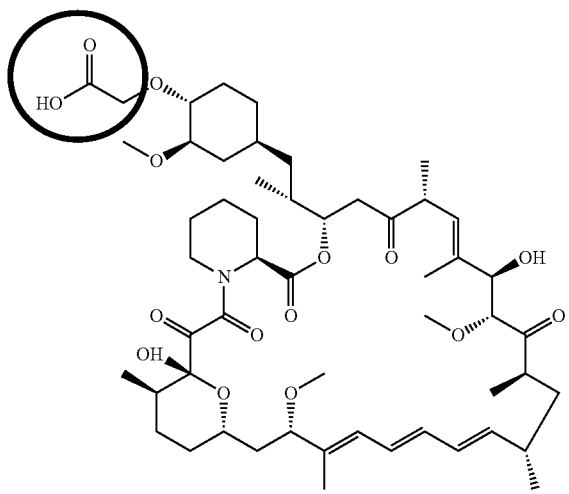

The everolimus-based drug including the carboxylic acid group at the end thereof as described above may be covalently bound to the surface-binding functional group. Here, the surface-binding functional group may include any one or more hydrophilic groups selected from a hydroxyl group, a carboxylic acid group, and the like. Preferably, the surface-binding functional group may include the hydroxyl group. As a preferable example, the carboxylic acid group at the end of the everolimus-based drug and the hydroxyl group of the surface-binding functional group may form and stably maintain a covalent bond of the drug by electrospinning.

In detail, the carboxylic acid group at the end of the everolimus-based drug and the hydrophilic group of the surface-binding functional group may be covalently bound to each other. Preferably, the covalent bond may include an ester bond. The hydroxyl group of the surface-binding functional group and the carboxylic acid group of the everolimus-based drug may be bound to each other via an ester bond (—O—C(=O)—) by a dehydration reaction, such that the drug may be more effectively and stably bound onto the titanium oxide layer of the stent.

As described above, since a strong bond between the everolimus-based drug and the surface-binding functional group of the stent may be stably maintained by electrospinning, it is possible to prevent initial excessive drug release and adjust a sustained drug release behavior for a long period of time without a polymer capable of causing side effects. Further, since a total content of the everolimus-based drug may be precisely controlled, even though a long period of time elapses, it is possible to minimize a fatal side effect that an effect of the drug is not exhibited due to rapid deterioration of a drug release effect.

In detail, in a stent manufactured by a physical coating method such as a dip coating method according to the related art, or the like, since a drug was physically attached to the stent, there was a disadvantage in that an initial release amount was large and most of the drug was initially released within a short time, and thus it was difficult to implement the sustained drug release effect.

Further, in a stent manufactured by an acid catalyst reaction in a liquid state or a reaction by a coupling agent according to the related art, since in theory, a drug is bound onto the stent only by a covalent bond, there is a disadvantage in that even though there is a need to initially release a predetermined amount or more of the drug, it is impossible to release the desired amount of the drug, but relatively, only a sustained release effect may be relatively implemented. Particularly, as the drug is bound only by the covalent bond, there was a problem in that it was impossible to load a high content of a drug due to a restricted surface area of the stent.

However, in the drug-eluting stent according to the present invention, since the everolimus-based drug is loaded on the stent by electrospinning and is directly bound onto the stent, the everolimus-based drug may be loaded with a high yield, and particularly, even though chemical stability of a drug is low, the drug may be loaded without deterioration of chemical stability. In addition, since the everolimus-based drug covalently bound to the surface-binding functional group of the stent and the everolimus-based drug physically bound onto the stent co-exist, a large amount of the everolimus-based drug may be loaded and a sustained release effect may be excellent. Further, the drug-eluting stent according to the present invention may induce release of a predetermined amount or more of the drug at an initial stage, and control a large amount of the drug to be continuously released at a later stage.

As a preferable example, the surface-binding functional group may be bound onto the nitrogen-doped titanium oxide layer by surface treatment with low-temperature plasma.

In detail, the nitrogen-doped titanium oxide layer may satisfy the following Correlation Equation 3. In the following Correlation Equation 3, $\theta_s$ is a contact angle of water with respect to a titanium oxide layer surface-treated with low-temperature plasma, and $\theta_0$ is a contact angle of water with respect to a nitrogen-doped titanium oxide layer that is not surface-treated with low-temperature plasma.

$$\theta_s/\theta_0 \leq 0.8 \qquad \text{[Correlation Equation 3]}$$

As a preferable example, the everolimus-based drug may be bound to the surface-binding functional group by electrospinning. In the drug-eluting stent of which the everolimus-based drug is covalently bound to the surface-binding functional group by electrospinning, a more stable binding may be formed than that in a drug-eluting stent by a physical coating method such as a dip coating method, or the like.

In general, a stent of which an everolimus-based drug is coated on a titanium oxide layer by a physical method such as the dip coating method, or the like, a thickness deviation of an everolimus-based drug layer may be large. For example, in the stent by the physical method such as the dip coating, or the like, when the closer to both ends of the stent, the thicker the layer, such that there was a problem in that a loading content of the everolimus-based drug per area of the stent was not uniform. Therefore, a release content and a release rate of the everolimus-based drug may be changed depending on an area position of the stent, such that it was impossible to precisely control a degree of release. In addition, since the release rate and release content are changed depending on each area position of the stent, an overall lifetime of the stent may be significantly deteriorated.

On the contrary, since in the stent of which the everolimus-based drug is coated on the titanium oxide layer by electrospinning, since the everolimus-based drug forms a more stable ester bond, the everolimus-based drug may be bound onto the stent while forming a more stable layer. Therefore, a drug release amount may be constantly and continuously maintained, and a drug release time may be maximized. As an example, the everolimus-based drug layer of the stent onto which the everolimus-based drug is bound by electrospinning may exist as a thin and uniform layer equal to or thinner than about ⅙ of a thickness of an everolimus-based drug layer bound to the stent by dip coating. Further, original structures of the titanium oxide layer and the everolimus-based drug may be stably maintained, respectively. In addition, since the drug-eluting stent according to the present invention has a uniform everolimus-based drug layer, a loading content of the everolimus-based drug may be further increased by an electrospinning method, such that even though a long period of time elapses, it is possible to minimize the fatal side effect that that the effect of the drug is not exhibited due to rapid deterioration of a drug release effect.

In the exemplary embodiment of the present invention, the drug-eluting stent may satisfy the following Correlation Equation 1, preferably, the following Correlation Equation 1-2. In the following Correlation 1 or 1-2, $R_{7d}$ is a cumulative elution amount of the everolimus-based drug eluted from the drug-eluting stent in a phosphate buffer saline solvent (pH 7.4) at 37° C. and 100 rpm for 7 days, and $R_A$ is a total loading amount of the everolimus-based drug loaded on the stent. The total loading amount is a total content of the everolimus-based drug formed on the titanium oxide layer of the stent by electrospinning. Here, a unit of the cumulative elution amount and the total loading amount is a mass unit.

$$R_{7d}/R_A \leq 0.85 \qquad \text{[Correlation Equation 1]}$$

$$R_{7d}/R_A \leq 0.8 \qquad \text{[Correlation Equation 1-2]}$$

$R_{7d}/R_A$ is a cumulative elution amount ratio of the everolimus-based drug for 7 days, and the drug-eluting stent satisfying Correlation Equation 1 has a cumulative elution amount ratio of 0.85 or less after 7 days, such that the drug-eluting stent may significantly suppress initial excessive elution.

Further, the drug-eluting stent may satisfy the following Correlation Equation 2, preferably, the following Correlation Equation 2-2. In the following Correlation 2 or 2-2, $R_{1d}$ is a cumulative elution amount of the everolimus-based drug eluted from the drug-eluting stent in the phosphate buffer saline solvent (pH 7.4) at 37° C. and 100 rpm for 1 day, and $R_A$ is the total loading amount of the everolimus-based drug loaded on the stent. The total loading amount is the total content of the everolimus-based drug formed on the titanium oxide layer of the stent by electrospinning. Here, a unit of the cumulative elution amount and the total loading amount is a mass unit.

$$R_{1d}/R_A \leq 0.30 \quad \text{[Correlation Equation 2]}$$

$$R_{1d}/R_A \leq 0.25 \quad \text{[Correlation Equation 2]}$$

$R_{1d}/R_A$ is an elution amount ratio of the everolimus-based drug for 1 day. In detail, the drug-eluting stent satisfying Correlation Equation 2 has a low average elution amount ratio of 0.25 or less for 1 day, such that the drug-eluting stent may significantly suppress initial excessive elution.

A test for measuring the elution amount may be performed by measuring absorbance at 278 nm using a UV-visible spectrophotometer, or the like, and in more detail, a test condition may be based on that in the elution test of Japanese Pharmacopeia.

A method of manufacturing a drug-eluting stent according to an exemplary embodiment of the present invention includes: electrospinning an everolimus-based drug on a nitrogen-doped titanium oxide layer on which a surface-binding functional group is formed to thereby form a covalent bond between the everolimus-based drug and the surface-binding functional group. In this case, the surface-binding functional group may be introduced onto the nitrogen-doped titanium oxide layer formed on a surface of the stent by surface-modification with low-temperature plasma.

More specifically, the method of manufacturing a drug-eluting stent may include: a) forming the nitrogen-doped titanium oxide layer on a surface of the stent, b) introducing the surface-binding functional group onto the titanium oxide layer to perform surface-modification, and c) electrospinning the everolimus-based drug to form the covalent bond between the everolimus-based drug and the surface-binding functional group.

Here, the covalent bond may be an ester bond. As described above, the everolimus-based drug is bound to the surface-binding functional group via the ester bond by electrospinning, such that a more uniform layer may be formed. Therefore, a drug release amount may be constantly and continuously maintained, and a drug release time may be maximized. Further, original structures of the titanium oxide layer and the everolimus-based drug may be stably maintained, respectively. In addition, it is possible to further increase a loading content of the everolimus-based drug, such that even though a long period of time elapses, it is possible to minimize a fatal side effect that an effect of the drug is not exhibited due to rapid deterioration of a drug release effect.

More specifically, in the drug-eluting stent according to the present invention, since the everolimus-based drug is loaded on the stent by electrospinning and is directly bound onto the stent, the everolimus-based drug may be loaded with a high yield, and particularly, the everolimus-based drug may be loaded without deterioration of chemical stability. In addition, since the everolimus-based drug covalently bound to the surface-binding functional group of the stent and the everolimus-based drug physically bound onto the stent co-exist, a large amount of the everolimus-based drug may be loaded and a sustained release effect may be excellent. Further, the drug-eluting stent according to the present invention may induce release of a predetermined amount or more of the drug in an initial stage, and control a large amount of the drug to be continuously released in a late stage.

Step a) is a step of forming the nitrogen-doped titanium oxide layer on the surface of the stent. More specifically, in step a), the nitrogen-doped titanium oxide layer may be formed on the surface of the stent using various methods known in the art. For example, various methods such as a plasma enhanced chemical vapor deposition method, a dip coating method, a physical vapor deposition method, an aerosol deposition method, and the like, may be used.

As a preferable example, a method of forming the nitrogen-doped titanium oxide layer on the surface of the stent in step a) may be a plasma enhanced chemical vapor deposition (PECVD) method. In the case of using the plasma enhanced chemical vapor deposition method, there is an advantage in that a more uniform layer may be formed, and if necessary, a significantly thin layer may be formed. In addition, it is possible to induce so that a more uniform layer is finally formed on the surface of the stent even though the stent is subjected to surface modification in step b) and binding of the everolimus-based drug by electrospinning in step c).

As a more specific example, step a) may include reacting a titanium precursor, nitrogen gas, and oxygen gas with each other to form the nitrogen-doped titanium oxide layer on the surface of the stent using the plasma enhanced chemical vapor deposition method. As the titanium precursor, any titanium precursor may be used as long as the titanium oxide layer may be formed. For example, the titanium precursor may include any one or two or more selected from titanium butoxide, tetraethylmethylamino titanium, titanium ethoxide, titanium (IV) isopropoxide, tetramethylheptadiene titanium, and the like. A reaction temperature may be 300 to 600° C., a reaction time may be 1 to 10 hours, and a discharge power may be 1 to 300 W. In this case, as carrier gas, inert gas such as argon, or the like, may be used, and a flow rate ratio of argon gas, oxygen gas, and nitrogen gas may be 100:5 to 30:1 to 10, respectively. However, the above-mentioned coating method of the nitrogen-doped titanium oxide layer is described by way of example, but the present invention is not limited thereto.

Step b) is a step of introducing the surface-binding functional group onto the nitrogen-doped titanium oxide layer formed on the stent in step a) to perform surface-modification. The surface-binding functional group is introduced onto the titanium oxide layer, thereby making it possible to stably induce the ester bond by electrospinning the everolimus-based drug in subsequent step c) as compared to a general physical coating method such as a dip coating method, or the like. Therefore, a more uniform layer may be formed, such that a drug release amount may be constantly and continuously maintained, and a drug release time may be significantly increased. As an example, in the case of using electrospinning, a thin and uniform everolimus-based drug layer equal to or thinner than about ⅙ of a thickness of an everolimus-based drug layer in the case of using dip coating. Further, original structures of the titanium oxide layer and the everolimus-based drug may be stably maintained, respectively.

As the surface-modification method in step b), any surface-modification method may be used as long as it may introduce the surface-binding functional group onto the titanium oxide layer, but a surface-treatment method using low-temperature plasma may be preferably used.

As a specific example, the surface-modification method using the low-temperature plasma in step b) may be performed in a plasma vacuum chamber, and the surface-binding functional group may be introduced onto the nitrogen-doped titanium oxide layer by introducing precursors such as water vapor ($H_2O$), mixed gas in which hydrogen and oxygen are mixed with each other, or the like, into the plasma vacuum chamber from an external introduction pipe connected to the plasma vacuum chamber in a low vacuum state of $1\times10^{-3}$ to 1 torr. A reaction temperature is not limited as long as the surface-binding functional group may be introduced onto the titanium oxide layer, a reaction time may be 5 minutes to 2 hours, and a plasma discharge power may be in a range of 1 to 300 W. In this case, as carrier gas, inert gas such as argon, or the like, may be used and a flow rate ratio of the precursor such as water vapor, or the like, and argon may be 100:10 to 60, respectively. However, the above-mentioned surface-modification method using low-temperature plasma is described by way of example, but the present invention is not limited thereto.

As described above, the end of the everolimus-based drug may include the carboxylic acid group so that the everolimus-based drug may be covalently bound to the surface-binding functional group including the hydrophilic group such as the hydroxyl group, the carboxylic acid group, or the like, on the nitrogen-doped titanium oxide layer of the stent.

Therefore, the method of manufacturing a drug-eluting stent may further include introducing the carboxylic acid group at the end of the everolimus-based drug. Further, if necessary, after the inducing of the carboxylic acid group, extracting the everolimus-based drug in which the carboxylic acid group is introduced with methylene chloride, water, or the like, to increase a purity may be further performed.

As a specific example, the introducing of the carboxylic acid group at the end of the everolimus-based drug may be a step of mixing the everolimus-based drug represented by Chemical Formula 1 and an organic acid in an alcohol solvent to synthesize the everolimus-based drug represented by Chemical Formula 2, in which the carboxylic acid group is introduced. Here, the organic acid may be malonic acid, or the like, and the alcohol may be methanol, or the like.

Step c) is a step of electrospinning the everolimus-based drug on the nitrogen-doped titanium oxide layer subjected to step b) to form the covalent bond.

In general, the everolimus-based drug is not strongly bound by the physical coating method such as the dip coating method according to the related art, or the like, and binding stability is low, such that drug release characteristics are significantly deteriorated, and a release maintenance time is also significantly short. However, in the case in which the electrospinning of the everolimus-based drug is performed in step c) on the titanium oxide layer surface-modified in step b), binding between the carboxylic acid group and the hydroxyl group existing in the everolimus-based drug and the titanium oxide layer may be effective induced, such that the everolimus-based drug and the titanium oxide layer may be stably covalently bound to each other.

In addition, in a stent manufactured by an acid catalyst reaction in a liquid state or a reaction by a coupling agent according to the related art, since in theory, a drug is bound onto the stent only by a covalent bond, there is a problem in that it is impossible to load the drug at a high content due to a restricted surface area of the stent bound only by the covalent bond.

On the contrary, in the case in which the everolimus-based drug is loaded on the stent by the electrospinning in step c), since the everolimus-based drug is directly bound onto the stent, the everolimus-based drug may be loaded at a high yield without deterioration of chemical stability. In addition, since the everolimus-based drug covalently bound to the surface-binding functional group of the stent and the everolimus-based drug physically bound onto the stent co-exist, a large amount of the everolimus-based drug may be loaded and a sustained release effect may be excellent. In addition, it is possible to control a large amount of the drug to be continuously released from an initial stage to a late stage.

As a specific example, the electrospinning in step c) may be performed by a general method known in the art. For example, the electrospinning may be performed by a method of spinning a mixture containing the everolimus-based drug and a solvent on the surface of the nitrogen-doped titanium oxide layer of the stent using a high-voltage generator. The solvent may be acetonitrile, or the like, and the mixture may further contain any one or more promoters selected from 4-dimethylaminopyridine (DMAP), 1-(3-dimethylaminopropyl)-3-ethyl carbodiimide (DAEC), and the like. Here, an applied voltage may be 1 to 15 kV, an air pressure may be 1 to 10 kgf/cm², a distance from a nozzle to the stent may be 10 to 15 cm, a rotation speed of the stent may be 50 to 100 rpm, a spray speed may be 60 µl/min, and the like. However, these conditions are provided by way of example, but the present invention is not limited thereto.

In the exemplary embodiment of the present invention, the everolimus-based drug may be a compound having functions of preventing thrombosis and restenosis, and the like, and include any one or more selected from everolimus and everolimus derivatives. A specific example of the everolimus derivative may include any one or two or more selected from biolimus A9, myolimus, novolimus, pimecrolimus, ridaforolimus, deoxorapamycin, tacrolimus FK 506, temsirolimus, zotarolimus, and the like.

In the exemplary embodiment of the present invention, as the stent, various stents known in the art may be used, and since characteristics of the stent such as a material, a shape, a length, a weight, and the like, of the stent may be suitably adjusted by those skilled in the art, the stent may be freely selected. Preferably, the stent has elasticity so as to have excellent mobility, and particularly, a stent which does not have corrosivity and is not harmful to a human body is preferable. For reference, specific examples of the stent are disclosed in Korean Patent Laid-Open Publication No. 10-2000-0069536, Korean Patent Laid-Open Publication No. 10-1999-0035927, Korean Patent Laid-Open Publication No. 10-1999-0087472, Korean Patent Laid-Open Publication No. 10-2002-0093610, Korean Patent Laid-Open Publication No. 10-2004-0055785, and the like.

As the material of the stent, biocompatible metals known in the art, metals in which various ingredients are bound to biocompatible metals, and the like, may be used without limitation. For example, the material may include biocompatible metals including any one metal selected from stainless steel, nitinol, tantalum, platinum, titanium, cobalt, chromium, molybdenum, and the like, or an alloy of two or more thereof. As a specific and preferable example, the material of the stent may include cobalt, chromium, an alloy thereof, and the like.

In the exemplary embodiment of the present invention, the method of manufacturing a drug-eluting coronary stent may further include, after step c), separating the stent to wash the stent. For example, this step may include a step of washing the stent with an organic solvent such as alcohols, washing the stent with deionized water several times, and drying the stent. Since the washing may be performed by a washing method known in the art and performed by those skilled in the art, and the washing method is not limited.

Hereinafter, the present invention will be described in detail through Examples, but they are provided only for describing of the present invention in more detail, and the scope of the present invention is not limited thereby.

Example 1

First, in order to form a nitrogen-doped titanium oxide layer on a surface of a stent, the nitrogen-doped titanium oxide layer was coated on a surface of a Co—Cr alloy stent (BMS) using a plasma enhanced chemical vapor deposition method, thereby manufacturing a titanium oxide layer-coated stent (N—$TiO_2$).

In detail, the Co—Cr alloy stent was fixed in a vacuum chamber to which a radiofrequency (RF) plasma generator generating plasma and a vacuum pump were connected using a titanium wire, and a temperature of the plasma chamber was maintained at 400° C. In addition argon gas (high-purity Ar gas, Azusanso, 99.999%) was used as carrier gas, and titanium(IV) isopropoxide (97%, Sigam-Aldrich, Co.) was used as a precursor. Here, the nitrogen-doped titanium oxide layer was coated on the surface of the Co—Cr alloy stent by reacting oxygen gas and nitrogen gas (high-purity $O_2/N_2$). In this case, a flow rate of the argon gas was 100 sccm, a flow rate of the oxygen gas was 16 sccm, a flow rate of the nitrogen gas was 4 sccm, and the reaction was carried out at a discharge power of 5 W for 4 hours.

In order to modify a surface of the titanium oxide layer-coated stent (N—$TiO_2$), a hydroxyl group was introduced onto the nitrogen-doped titanium oxide layer of the stent using a low-temperature plasma process, thereby manufacturing a surface-modified stent (N—$TiO_2H_2O$+Ar treated).

In detail, after fixing the titanium oxide layer-coated stent (N—$TiO_2$) in a tube type low-temperature plasma reactor made of Pyrex and filling distilled water in a bubbler, the hydroxyl group was introduced onto the nitrogen-doped titanium oxide layer of the stent ((N—$TiO_2$) using a low-temperature plasma process of maintaining a flow rate of water vapor at 10 sccm and a flow rate of the argon gas at 3.3 sccm and performing a reaction at a discharge power of 30 W for 15 minutes.

A contact angle of a surface of the surface-modified stent (N—$TiO_2H_2O$+Ar treated) with respect to water was measured, and the result was illustrated in FIG. 4 together with contact angles of the surfaces of the Co—Cr alloy stent (BMS) and the titanium oxide layer-coated stent (N—$TiO_2$) with respect to water.

A drug-eluting stent of which an everolimus-based drug (EVL-COOH) was formed on the surface of the nitrogen-doped titanium oxide layer was manufactured by electrospinning a drug mixture solution in which an acetonitrile solution (0.8 mg/ml) containing the everolimus-based drug (0.006 mmol) represented by Chemical Formula 2 of which a carboxylic acid group was introduced at an end, and a promoter containing 4-dimethylaminopyridine (0.006 mmol) and 1-(3-dimethylaminopropyl)-3-ethylcarbodiimide (0.03 mmol) were mixed a weight ratio of 1:1 on the surface of the surface-modified stent (N—$TiO_2H_2O$+Ar treated), and allowing the carboxylic acid group of the everolimus-based drug (EVL-COOH) to be bound to the hydroxyl group on the surface of the stent.

In order to evaluate drug release characteristics of the drug-eluting stent, an elution test was performed using phosphate buffer saline (PBS, 3 ml, pH 7.4) at a rotation speed of 100 rpm and an elution temperature of 37° C. After initiating the elution test, an elution solution was collected every day (every 24 hour), absorbance thereof was measured using a UV-visible spectrophotometer at a wavelength of 278 nm, and an elution amount was calculated. The results were illustrated in FIG. 5.

Comparative Example 1

The everolimus-based drug (EVL-COOH) was coated on the surface of the surface-modified stent (N—$TiO_2H_2O$+Ar treated) of Example 1 using a dip coating method of dipping the surface-modified stent in the drug mixture solution of Example 1.

FIG. 1 is a graph illustrating data obtained by measuring surfaces of the drug-eluting stents according to Example 1 and Comparative Example 1 using Fourier transform infrared spectroscopy (FT-IR/ATR). As illustrated in FIG. 1, it may be appreciated that there was a significant difference between a spectrum in Comparative Example 1 in which the everolimus-based drug (EVL-COOH) was coated by the dip coating method and a spectrum of everolimus-based drug powder (EVL-COOH powder) of FIG. 2. On the contrary, it may be appreciated that a spectrum in Example 1 in which the everolimus-based drug was bound onto the surface using the electrospinning method was almost the same spectrum as that of the everolimus-based drug powder (EVL-COOH powder) of FIG. 2.

Further, it may be appreciated that at the time of comparing the spectra in Comparative Example 1 and Example 1 in FIG. 1, in Example 1, a peak indicating an ester bond was more strongly shown as compared to Comparative Example 1. Therefore, it may be appreciated that the everolimus-based drug bound via the ester bond per unit area was significantly increased. Therefore, even though a long period of time elapses, it is possible to suppress and minimize a fatal side effect that an effect of the drug is not exhibited due to rapid deterioration of a drug release effect.

FIG. 2 is a graph illustrating and comparing data obtained by measuring the surface of the drug-eluting stent according to Example 1 and the everolimus-based drug powder (EVL-COOH powder) using FT-IR/ATR. As illustrated in FIG. 2, it may be confirmed that in, the everolimus-based drug (EVL-COOH) was uniformly and stably loaded (bound) on the surface of the drug-eluting stent according to Example 1, such that almost the same spectrum as that of the everolimus-based drug powder (EVL-COOH powder) was shown.

The following Table 1 indicates a total loading amount of the drug bound onto the surface of the drug-eluting stent according to Example 1 per coating area and a total content of the drug coated onto the surface of the drug-eluting stent according to Comparative Example 1 per coating area. As illustrated in the following Table 1, it may be appreciated that in Example 1, the loading content was 0.1735 μg/$mm^2$, but in Comparative Example 1, the loading content was 1.1308 μg/$mm^2$, such that a difference between the loading contents was about 6 times. Therefore, it may be appreciated that it was difficult to form a uniform layer by a physical coating method such as the dip coating method, and the like, and it may be expect that the elution amount and an elution rate of the everolimus-based drug will be different depending on an area position of the stent. Therefore, it may be appreciated that it is impossible to precisely control the elution amount of the everolimus-based drug coated on the titanium oxide layer of the stent as in the electrospinning method.

That is, in the case of using a chemical binding method using electrospinning, the everolimus-based drug may be formed to have a more uniform layer on the titanium oxide layer of the stent as compared to the physical coating method such as the dip coating method, or the like.

TABLE 1

| | Total Loading Amount of Drug Per Coating Area (μg/mm²) |
|---|---|
| Example 1 | 0.1735 μg/mm² |
| Comparative Example 1 | 1.1308 μg/mm² |

FIG. 3 is a graph illustrating contact angles of surfaces of the initially untreated Co—Cr alloy stent (BMS), the titanium oxide layer-coated stent (N—TiO₂), and the surface-modified stent (N—TiO₂H₂O+Ar treated) in Example 1 with respect to water and FIG. 4 is images indicating the contact angles. As illustrated in FIGS. 3 and 4, it may be indirectly appreciated that in the surface of the surface-modified stent (N—TiO₂H₂O+Ar treated), a degree of introduction of the surface-binding function group including the hydroxyl group was high. Therefore, conversely, it may be appreciated that the carboxylic acid group at the end of the everolimus-based drug (EVL-COOH) and the surface-binding functional group including the hydroxyl group were bound to each other via the ester bond by subsequent electrospinning, thereby making it possible to maintain a strong bond.

FIG. 5 is a graph illustrating results obtained by measuring amounts of the everolimus-based drug eluted from the drug-eluting stents according to Example 1 and Comparative Example 1 per unit time (day). It may be appreciated from FIG. 5 that in Example 1 in which the electrospinning method was used, the elution rate of the everolimus-based drug was significantly delayed as compared to Comparative Example 1 in which the dip coating method was used. Therefore, it may be appreciated that an effect caused by release of the everolimus-based drug may be maintained for a long period of time.

In detail, it may be confirmed that in Example 1, an average release rate $((R_{1d}/R_A)/(t_{1d}))$ of the everolimus-based based drug for a first day was 0.22, but in Comparative Example 1, an average release rate $((R_{1d}/R_A)/t_{1d})$ of the everolimus-based drug for a first day was 0.72.

Further, in view of a cumulative release amount, it may be appreciated that in Example 1, a cumulative release amount $(R_{7d}/R_A)$ based on 7 days was 0.8, but in Comparative Example 1, a cumulative release amount $(R_{7d}/R_A)$ based on 7 days was 0.95.

Therefore, it may be appreciated that in Comparative Example 1, initially, the everolimus-based drug was mostly lost and thereafter, a drug release effect was insignificant, but in Example 1, an initial loss of the everolimus-based drug was relatively minimized, such that the drug release effect may be maintained for a long period of time.

In the drug-eluting coronary stent and the method of manufacturing the same according to the present invention, it is possible to effectively bind the everolimus-based drug to the stent without using the polymer causing various side effects such as local inflammation, suppression of re-endothelialization, and the like, by using surface modification and electrospinning.

Further, in the drug-eluting coronary stent and the method of manufacturing the same according to the present invention, the total content of the everolimus-based drug bound onto the titanium oxide layer may be precisely controlled, such that initial excessive drug release may be prevented, the sustained drug release behavior may be adjusted for a long period of time, and the uniform layer of the everolimus-based drug may be formed.

Furthermore, in the drug-eluting coronary stent according to the present invention, the total content of the everolimus-based drug may be significantly increased, such that even though a long period of time elapses, it is possible to minimize the fatal side effect that the effect of the drug is not exhibited due to rapid deterioration of the drug release effect.

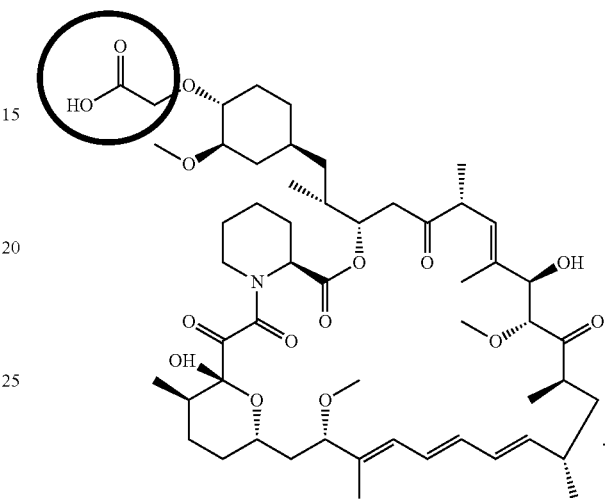

What is claimed is:
1. A method of manufacturing a drug-eluting stent, the method comprising:
   a) forming a nitrogen-doped titanium oxide layer on a surface of a stent;
   b) introducing a surface-binding functional group including a hydroxyl group onto the titanium oxide layer to perform surface-modification;
   c) preparing an everolimus-based drug of which a carboxylic acid group is formed at an end; and
   d) electrospinning a mixture containing the everolimus-based drug of which a carboxylic acid group is formed at an end and a solvent on the surface-modified titanium oxide layer,
   wherein the drug-eluting stent contains the everolimus-based drug bound onto the stent via an ester bond and the everolimus-based drug physically attached to the stent, but does not contain a polymer
   wherein the everolimus-based drug of which the carboxylic acid group is formed at the end is prepared by mixing an everolimus-based drug represented by the following Chemical Formula 1 and an organic acid in an alcohol solvent

Chemical Formula 1

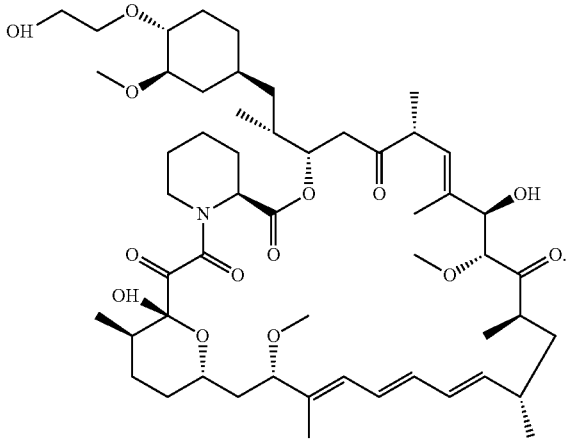

2. The method of claim 1, wherein the drug-eluting stent satisfies the following Correlation Equation 1:

$R_{7d}/R_A \leq 0.85$   Correlation Equation 1 here, $R_{7d}$ is a cumulative elution amount of the everolimus-based drug eluted from the drug-eluting stent in a phosphate buffer saline solvent at pH 7.4, 37° C. and 100 rpm for 7 days, $R_A$ is a total loading amount of the everolimus-based drug loaded on the stent, and the unit of the cumulative elution amount and the total loading amount is a mass unit.

3. The method of claim 2, wherein the drug-eluting stent satisfies the following Correlation Equation 2:

$$R_{1d}/R_A \leq 0.3 \qquad \text{Correlation Equation 2}$$

here, $R_{1d}$ is a cumulative elution amount of the everolimus-based drug eluted from the drug-eluting stent in the phosphate buffer saline solvent at pH 7.4, 37° C. and 100 rpm for 1 day, $R_A$ is the total loading amount of the everolimus-based drug loaded on the stent, and a unit of the cumulative elution amount and the total loading amount is a mass unit.

4. The method of claim 1, wherein the surface-binding functional group is formed on the nitrogen-doped titanium oxide layer by surface-treatment with low-temperature plasma, and the nitrogen-doped titanium oxide layer satisfies the following Correlation Equation 3:

$$\theta_s/\theta_0 \leq 0.80 \qquad \text{Correlation Equation 3}$$

here, $\theta_s$ is a contact angle of water with respect to the titanium oxide layer surface-treated with the low-temperature plasma, and $\theta_0$ is a contact angle of water with respect to a nitrogen-doped titanium oxide layer that is not surface-treated with the low-temperature plasma.

5. The method of claim 1, wherein the solvent is acetonitrile.

6. The method of claim 1, wherein the mixture further contains any one or more promoters selected from the group consisting of 4-dimethylaminopyridine and 1-(3-dimethylaminopropyl)-3-ethyl carbodiimide.

7. The method of claim 1, wherein the everolimus-based drug of which the carboxylic acid group is formed at the end is Represented by the following Chemical Formula 2;

Chemical Formula 2